(12) United States Patent
Langston

(10) Patent No.: US 8,613,706 B2
(45) Date of Patent: Dec. 24, 2013

(54) COAXIAL DUAL LUMEN PIGTAIL CATHETER

(76) Inventor: Phil Langston, Mounds, OK (US)

( * ) Notice: Subject to any disclaimer, the term of this patent is extended or adjusted under 35 U.S.C. 154(b) by 1452 days.

(21) Appl. No.: 11/890,070

(22) Filed: Aug. 3, 2007

(65) Prior Publication Data

US 2008/0027334 A1   Jan. 31, 2008

Related U.S. Application Data

(62) Division of application No. 10/797,583, filed on Mar. 10, 2004, now abandoned.

(51) Int. Cl.
*A61B 5/02* (2006.01)
*A61M 25/00* (2006.01)

(52) U.S. Cl.
USPC .............. 600/486; 600/481; 600/485; 604/43

(58) Field of Classification Search
USPC .................... 600/481, 485, 486; 604/43
See application file for complete search history.

(56) References Cited

U.S. PATENT DOCUMENTS

| | | | |
|---|---|---|---|
| 4,747,840 A * | 5/1988 | Ladika et al. ................. | 604/532 |
| 4,770,652 A | 9/1988 | Mahurkar | |
| 4,777,951 A * | 10/1988 | Cribier et al. ................ | 606/194 |
| 4,961,731 A | 10/1990 | Bodicky et al. | |
| 5,009,234 A * | 4/1991 | Alt ................................ | 600/485 |
| 5,016,808 A | 5/1991 | Heil, Jr. et al. | |
| 5,037,403 A | 8/1991 | Garcia | |
| 5,041,084 A | 8/1991 | DeVries et al. | |
| 5,052,998 A | 10/1991 | Zimmon | |
| 5,308,318 A | 5/1994 | Plassche, Jr. | |
| 5,346,471 A | 9/1994 | Raulerson | |
| 5,380,270 A | 1/1995 | Ahmadzadeh | |
| 5,380,276 A | 1/1995 | Miller et al. | |
| 5,480,380 A | 1/1996 | Martin | |
| 5,480,392 A | 1/1996 | Mous | |
| 5,683,640 A | 11/1997 | Miller et al. | |
| 5,961,485 A | 10/1999 | Martin | |
| 5,976,103 A | 11/1999 | Martin | |
| 6,048,332 A | 4/2000 | Duffy et al. | |
| 6,332,892 B1 | 12/2001 | Desmond, III et al. | |
| 6,413,228 B1 | 7/2002 | Hung et al. | |
| 6,508,789 B1 | 1/2003 | Sinnott et al. | |
| 6,656,146 B1 | 12/2003 | Clayman et al. | |
| 2002/0173693 A1 * | 11/2002 | Landesberg .................... | 600/16 |
| 2003/0195409 A1 * | 10/2003 | Seitz et al. .................... | 600/407 |
| 2003/0199779 A1 * | 10/2003 | Muhlenberg et al. ......... | 600/513 |
| 2004/0254483 A1 * | 12/2004 | Zdeblick et al. .............. | 600/486 |
| 2007/0161914 A1 * | 7/2007 | Zdeblick et al. .............. | 600/486 |
| 2007/0219591 A1 * | 9/2007 | Zdeblick et al. ................ | 607/17 |

* cited by examiner

*Primary Examiner* — Michael Kahelin
*Assistant Examiner* — Karen Toth
(74) *Attorney, Agent, or Firm* — Patterson Thuente Pedersen, P.A.

(57) ABSTRACT

A method of measuring differential pressure between a left ventricle and an aorta across an aortic valve for diagnosis of aortic stenosis using a coaxial dual lumen pigtail catheter that utilizes coaxial construction incorporating a thin wall guiding catheter technology for the outer lumen and using a strong braided diagnostic technology for the central lumen to accommodate high-pressure injections. The catheter includes a manifold body to provide for connection to each of the dual lumens. The distal end of the coaxial dual lumen pigtail catheter tapers to a more flexible portion that is perforated by spiral side holes to provide for more undistorted pressure readings in the left ventricle. The coaxial dual lumen pigtail catheter also utilizes proximal straight sideholes at the end of the dual lumen portion and a taper between the dual lumen portion and the single lumen portion.

7 Claims, 3 Drawing Sheets

COAXIAL DUAL LUMEN PIGTAIL CATHETER

CLAIM TO PRIORITY

This application is a divisional of U.S. patent application Ser. No. 10/797,583 entitled Coaxial Dual Lumen Pigtail Catheter filed Mar. 10, 2004 now abandoned, the entire contents of which are incorporated herein by reference.

FIELD OF THE INVENTION

The present invention relates generally to the field of cardiac catheters. More specifically, the invention relates to cardiac catheters for performing procedures for the testing of aortic stenosis.

BACKGROUND OF THE INVENTION

Aortic stenosis is a condition in which the aortic valve has become stenotic (narrowed) and does not open normally. The aortic valve is located between the left ventricle of the heart and the aortic arch. The aortic arch leads to the ascending and descending aorta as well as other major blood vessels and is the main blood vessel that supplies oxygen rich blood to the rest of the body. When the aortic valve is stenotic, the ability of the left ventricle to pump blood out of the heart into the aorta and other arteries is impaired. The body's organs including the brain may then receive an insufficient supply of oxygen rich blood and blood may tend to back-up into the lungs causing shortness of breath.

The aortic valve is a tricuspid valve. That is, it has three leaflets or flaps that open and close. The function of the aortic valve is to allow blood to flow only out of the left ventricle and into the aorta when the left ventricle is contracting. When the heart muscle relaxes, the aortic valve closes, thus preventing blood from the aorta from flowing back into the left ventricle. When a patient has aortic stenosis, the leaflets of the aortic valve become thickened and calcified. Historically, a common cause of aortic stenosis was patients who had rheumatic fever during childhood. Other patients developed symptoms of aortic stenosis when they are in their 40's or 50's because of a genetically determined defect in which the aortic valve has two leaflets instead of three. By far, the most common cause of aortic stenosis is age related degeneration and calcification of the aortic valve. Typically, degenerative aortic stenosis begins to manifest symptoms when patients are more than 70 years old.

When the aortic valve becomes stenotic, the volume of blood pumped out of the left ventricle is reduced. The heart tissue then tends to hypertrophy to compensate for the increased effort necessary to pump blood out of the left ventricle. This ventricular hypertrophy leads to an enlarged heart. Ultimately, the left ventricle looses flexibility, tends to dilate and becomes even less efficient at pumping blood into the aorta. In some cases, the aortic valve becomes so stenotic that blood flow to the brain is dramatically reduced causing syncope. In addition, aortic stenosis patients often suffer from angina. Finally, patients with aortic stenosis tend to demonstrate shortness of breath because of the accumulation of blood in the lungs. Patients with severe aortic stenosis may require replacement of the aortic valve with a prosthetic heart valve.

One way to gauge the severity of aortic stenosis is to measure the pressure differential between the left ventricle and the aortic arch, across the aortic valve. Measuring differential pressure across the aortic valve to diagnosis aortic stenosis is a known procedure. One such technique for measuring differential pressures across the aortic valve utilizes a catheter that has an eight French diameter along its entire length and two parallel side-by-side lumens of unequal size. This catheter incorporates a perforated metal plate in the distal segment of the smaller lumen that allows fluid communication for measuring pressure in the aorta. The larger lumen of this catheter incorporates distal side holes that allows fluid communication for measuring pressure in the left ventricle. The smaller lumen is perforated on one side only and can lead to distorted pressure reading if the perforations impinge on the wall of the aorta as the pressure wave of aortic systole moves past the catheter. The side-by-side arrangement of the catheter tends to make the catheter less flexible and more difficult to maneuver. In addition, the durometer of the eight French distal tip is not always soft enough to conform to a guide wire.

Pigtail catheters are known in the art. A pigtail is a coiled or spiral portion at the terminal end of a catheter. The coil generally approximates three hundred sixty degrees but may be somewhat more or less than this value. A pigtail design presents a blunt, smooth, resilient end to body tissue into which it comes in contact reducing the risk of damage to tissues that the end of the catheter comes into contact with.

It would be a benefit to the diagnostic arts if there was available a differential pressure measuring catheter that was flexible enough to consistently conform to a guide wire and whose pressure measuring qualities were less effected by impingement on the vascular tissues.

SUMMARY OF THE INVENTION

The coaxial dual lumen pigtail catheter for performing testing in aortic stenosis addresses the above problems. The invention utilizes coaxial construction incorporating a thin wall extrusion for the outer lumen and using a strong braided extrusion for the central lumen and high-pressure injections. The catheter of the present invention includes a manifold body to provide for connection to each of the two lumens. The distal end of the coaxial dual lumen pigtail catheter tapers to a more flexible portion that is perforated by spiral side holes around at least a substantial portion of the circumference of the catheter to provide for less distorted pressure readings and to allow for perfusion into the left ventricle.

The coaxial dual lumen pigtail catheter of the present invention generally includes a dual lumen portion, single lumen portion and a pigtail portion. Preferably, the dual lumen portion is sized to be either an eight French or more preferably seven or even six French in diameter. Preferably, the single lumen portion has a five French diameter and the pigtail portion has a five French diameter. The coaxial dual lumen pigtail catheter utilizes proximal straight sideholes at the end of the dual lumen portion and a taper between the dual lumen portion and the single lumen portion. At the distal end of the single lumen portion, but proximal to the pigtail are located additional sideholes. These sideholes provide a conduit for taking a pressure measurement within the left ventricle as well as providing a conduit for the injection of diagnostic fluids, if necessary. Desirably, the sideholes are arranged in a spiral pattern around the single lumen portion.

DETAILED DESCRIPTION OF THE INVENTION

Figure 1:
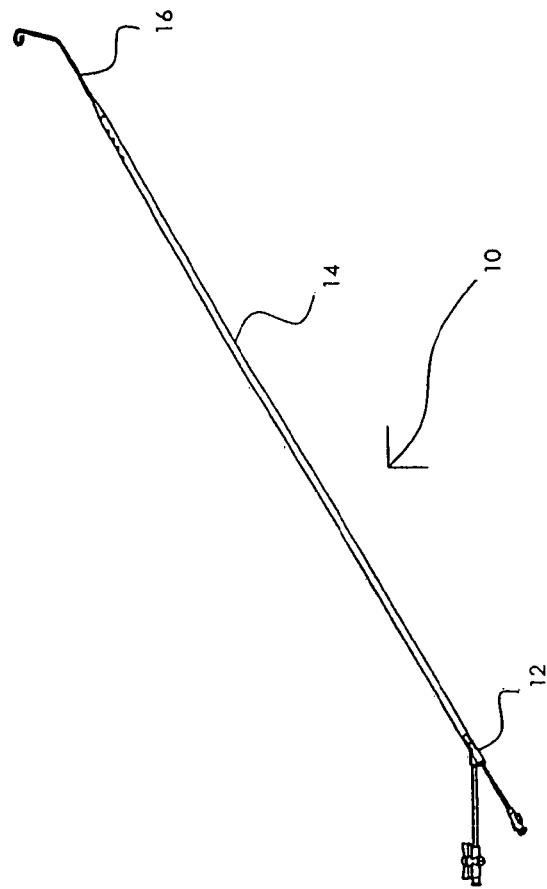
FIG. 1 is a perspective view of a coaxial dual lumen pigtail catheter.

Referring to FIG. 1, the coaxial dual lumen pigtail catheter 10 (catheter 10) generally includes manifold portion 12, dual lumen portion 14 and single lumen portion 16.

Figure 2:
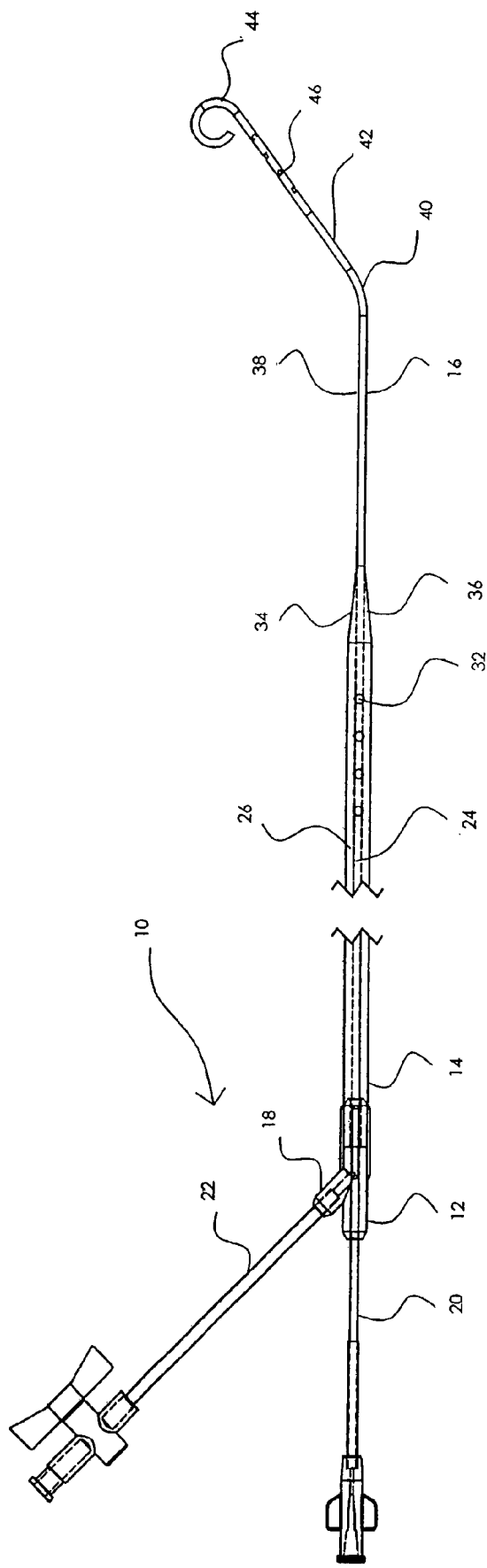
FIG. 2 is a plan view of the coaxial dual lumen pigtail catheter of the present invention, including phantom lines showing the interior lumen.
Figure 4:
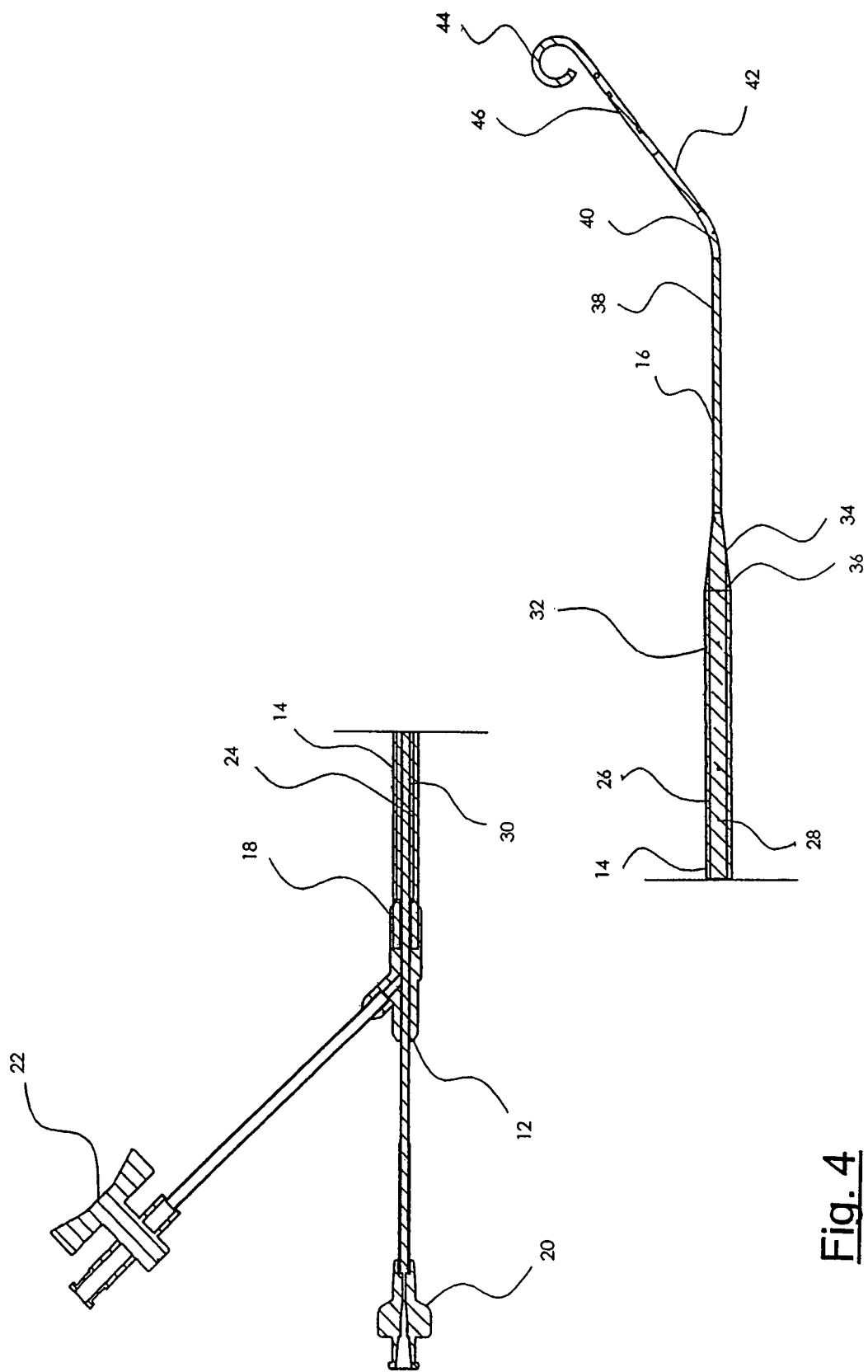
FIG. 4 is a sectional view of the coaxial dual lumen pigtail catheter.

Manifold portion 12 includes manifold body 18, first connector 20 and second connector 22. As best seen in FIGS. 2 and 4, first connector 20 and second connector 22 are both connected to manifold body 18. First connector 20 is connected to inner lumen 24. Second connector 22 is in fluid communication with outer lumen 26. Thus, manifold body 18 serves to provide for a transition from separate non-coaxial lumens of first connector 20 and second connector 22 to the coaxial lumens that extend through dual lumen portion 14.

Figure 3:
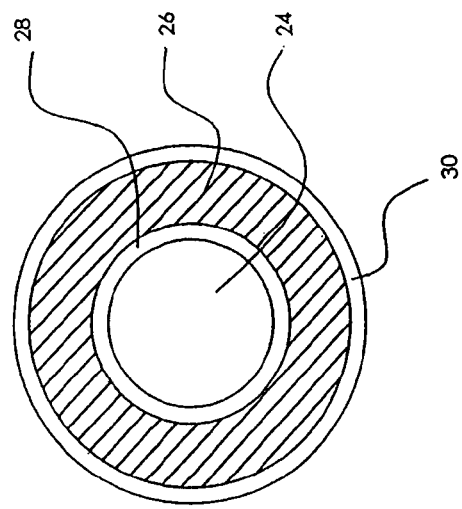
FIG. 3 is a cross sectional view of the coaxial dual lumen pigtail catheter.

Referring to FIG. 3, as indicated above, dual lumen portion 14 defines inner lumen 24 and outer lumen 26. Inner lumen 24 is defined by inner lumen wall 28. Outer lumen 26 is defined by the space between inner lumen wall 28 and outer lumen wall 30. Preferably, inner lumen wall 28 is formed from strong braided diagnostic tubing for high-pressure injections. Desirably, outer lumen wall is formed from thin wall extrusion. Desirably, outer lumen wall has a diameter of at most eight French and preferably seven or six French. Inner lumen wall 28, for example, may have an inside diameter at least 0.038 inches to accept a standard guidewire. The inner lumen wall 28 should be sufficient to withstand high pressure injections at pressures up to 1200 pounds per square inch which are utilized in diagnostic procedures.

Referring again to FIGS. 2 and 4, the distal end of dual lumen portion 14 is pierced by at least two side holes 32. Desirably, straight side holes 32 are distributed over an area covering approximately the distal four centimeters of the dual lumen portion 14, to provide for accuracy in measurement.

The juncture 34 between dual lumen portion 14 and single lumen portion 16 desirably includes a gradual taper 36.

Single lumen portion 16 generally includes first straight portion 38, bend 40, second straight portion 42 and pigtail 44. First straight portion 38 desirably extends for about eight centimeters distal from the beginning of taper 36. Desirably, single lumen portion 16 is soft enough to conform to a guide wire and is about five French in diameter.

Bend 40 begins at the distal end of first straight portion 38 and desirably is about 145 degrees. Second straight portion 42 extends distally from bend 40. Second straight portion 42 is pierced by spiral sideholes 46. Desirably, spiral sideholes 46 are distributed over a section of second straight portion 42 about two centimeters in length and are distributed in a spiral pattern that makes at least a substantial portion of one turn around the circumference of second straight portion 42. Preferably, spiral sideholes 46 encircle the second straight portion 42 approximately twice over the desired length.

Pigtail 44 extends distally from the termination of second straight portion 42. Desirably, pigtail 44 is about two centimeters or less in diameter. Pigtail 44 is a spiral coil shape extending around approximately 360 degrees. Desirably, pigtail 44 is sufficiently flexible to be straightened by the passage of a guide wire to allow the pigtail 44 to be passed through the aortic valve and into the left ventricle.

Desirably, the overall length of coaxial dual lumen pigtail catheter 10 is at least 110 centimeters from manifold body 18 to the end of pigtail 44.

Straight side holes 32 are in fluid communication with outer lumen 26. Spiral sideholes 46 are in fluid communication with inner lumen 24.

In operation, coaxial dual lumen pigtail catheter 10 is typically inserted percutaneously into the femoral artery. A guide wire (not shown) is introduced into a puncture in the femoral artery and advanced through the aorta into the left ventricle. The coaxial dual lumen pigtail catheter 10 is advanced along the guide wire while it conforms to the shape of the guide wire and into the left ventricle. The guide wire is then withdrawn, leaving the coaxial dual lumen pigtail catheter in place so that the pigtail 44 resumes its shape in the left ventricle. The second straight portion 42 is in the left ventricle and the first straight portion and dual lumen portion are in the aorta. A pressure measuring device (not shown) of conventional design may then be connected to first connector 20 and second connector 22 to measure the differential pressure between the left ventricle on the proximal side of the aortic valve and the aorta on the distal side of the aortic valve. Simultaneous pressures can be obtained to obtain a diagnostic pressure gradient across the valve by comparing the systolic peaks in the ventricle and the aorta.

In addition, radio opaque fluid may be injected through the inner lumen 26 to perfuse through spiral side holes 46 into the left ventricle. A physician may then observe the flow of radio opaque fluid by fluoroscopy of the heart across the aortic valve.

The pigtail 44 serves both to anchor the single lumen portion 16 within the left ventricle and to present a blunt rounded structure to the internal ventricular wall to reduce the risk of trauma to the ventricular wall.

The present invention may be embodied in other specific forms without departing from the spirit of the essential attributes thereof, therefore, the illustrated embodiments should be considered in all respects as illustrative and not restive, reference being made to the appended claims rather than to the foregoing description to indicate the scope of the invention.

The invention claimed is:

1. A method of measuring differential pressure between a left ventricle of a heart and an aorta of a patient across an aortic valve for diagnosis of aortic stenosis, the method comprising:

creating a percutaneous access to a major artery in a human body of the patient;

inserting a guidewire into the major artery and guiding the guidewire from the major artery through an aorta and into a left ventricle of the heart, the aorta and the left ventricle being separated by an aortic valve;

inserting a coaxial dual lumen pigtail catheter having a dual lumen portion and a single lumen portion along the guidewire, the single lumen portion having a first proximal straight portion, a second distal straight portion, a bend between the first proximal straight portion and the second distal straight portion and a pigtail portion, the single lumen portion having a constant fixed diameter along its length and the dual lumen portion having exactly two coaxial lumens along an entire length extending from a manifold to the single lumen portion;

advancing the coaxial dual lumen catheter until the pigtail portion of the single lumen portion and the second straight portion of the catheter are positioned in the left ventricle while the first straight portion of the single lumen portion bridges the aortic valve and extends into the aorta and the dual lumen portion is positioned partially in the aorta and extends to the exterior of the patient;

withdrawing the guidewire from the catheter;

operably coupling a pressure measuring device in fluid communication with a first lumen and a second lumen of the catheter, the first lumen being in fluid communication with the left ventricle and the second lumen being in fluid communication with the aorta;

obtaining simultaneous pressure measurements from both the aorta and the left ventricle while the first straight portion of the single lumen portion bridges the aortic valve; and determining a diagnostic pressure gradient across the valve by comparing the pressure measurements in the left ventricle and the aorta.

2. The method as claimed in claim 1, in which the determination of the diagnostic pressure gradient further comprises determining the diagnostic pressure gradient across the valve by comparing systolic peaks in the ventricle and the aorta.

3. The method as claimed in claim 1, further comprising measuring differential pressure between the ventricle and the aorta.

4. The method as claimed in claim 1, further comprising injecting a marker fluid through the first lumen into the ventricle.

5. The method as claimed in claim 4, further comprising observing the marker fluid whereby flow across the aortic valve is observed.

6. The method as claimed in claim 4, wherein the marker fluid comprises a radio opaque fluid.

7. The method as claimed in claim 6, further comprising observing the radio opaque fluid via fluoroscopy.

\* \* \* \* \*